(12) United States Patent
D'Angelo et al.

(10) Patent No.: US 12,005,134 B2
(45) Date of Patent: Jun. 11, 2024

(54) COMPOSITION FOR STIMULATING FACIAL HAIR GROWTH AND METHODS OF MANUFACTURING A COMPOSITION FOR STIMULATING FACIAL HAIR GROWTH

(71) Applicant: Abe Pharmaceutical, Philadelphia, PA (US)

(72) Inventors: Nicholas D'Angelo, Philadelphia, PA (US); Matthew Weiss, Philadelphia, PA (US)

( * ) Notice: Subject to any disclaimer, the term of this patent is extended or adjusted under 35 U.S.C. 154(b) by 0 days.

(21) Appl. No.: 17/855,206

(22) Filed: Jun. 30, 2022

(65) Prior Publication Data
US 2023/0000746 A1 Jan. 5, 2023

Related U.S. Application Data

(60) Provisional application No. 63/216,712, filed on Jun. 30, 2021.

(51) Int. Cl.
*A61K 8/49* (2006.01)
*A61K 8/34* (2006.01)
*A61K 8/92* (2006.01)
*A61Q 7/00* (2006.01)

(52) U.S. Cl.
CPC ............ *A61K 8/4953* (2013.01); *A61K 8/34* (2013.01); *A61K 8/92* (2013.01); *A61Q 7/00* (2013.01)

(58) Field of Classification Search
CPC .......... A61K 8/34; A61K 8/4953; A61K 8/92; A61K 8/342; A61K 8/922; A61K 8/97; A61K 2800/22; A61K 2800/884; A61K 2800/92; A61K 8/20; A61K 8/22; A61K 8/44; A61K 8/4913; A61K 8/58; A61K 8/63; A61Q 7/00; A61Q 5/00; A61Q 11/00; A61C 17/18; A61P 1/02; A61P 35/00
See application file for complete search history.

(56) References Cited

U.S. PATENT DOCUMENTS

| | | | |
|---|---|---|---|
| 5,407,944 A * | 4/1995 | Goldman | A61Q 7/00 514/880 |
| 5,753,263 A * | 5/1998 | Lishko | C12Y 110/03001 514/20.7 |
| 2007/0093462 A1 | 4/2007 | Rogers et al. | |
| 2007/0160562 A1 * | 7/2007 | Brinkenhoff | A61K 8/37 424/70.22 |
| 2012/0156144 A1 * | 6/2012 | Tamarkin | A61P 31/10 424/43 |
| 2016/0263225 A1 | 9/2016 | Zakrewsky et al. | |
| 2017/0319751 A1 | 11/2017 | Milbocker et al. | |
| 2018/0208618 A1 | 7/2018 | Ono et al. | |
| 2020/0163885 A1 * | 5/2020 | Won | A61K 38/1709 |

FOREIGN PATENT DOCUMENTS

| | | | |
|---|---|---|---|
| JP | 2013528653 A5 * | 7/2014 | ............ A61P 17/14 |
| WO | 1991016030 | 10/1991 | |
| WO | 2004078163 | 1/2005 | |
| WO | 2019183142 | 9/2019 | |
| WO | WO2019200027 A1 * | 10/2019 | ............ A61K 8/49 |
| WO | 2019217854 | 11/2019 | |
| WO | 2020166678 | 8/2020 | |
| WO | 2020205409 | 10/2020 | |
| WO | 2021050953 | 3/2021 | |

OTHER PUBLICATIONS

JP2013528653A5 translation (Year: 2013).*
Islam et al., Ionic Liquid-In-Oil Microemulsions Prepared with Biocompatible Choline Carboxylic Acids for Improving the Transdermal Delivery of a Sparingly Soluble Drug, Dec. 31, 2020.

* cited by examiner

*Primary Examiner* — Audrea B Coniglio
*Assistant Examiner* — Audrea Buckley
(74) *Attorney, Agent, or Firm* — Caldwell Intellectual Property Law

(57) ABSTRACT

A composition for stimulating facial hair growth includes a vasodilator including a medication that stimulates cell proliferation of a plurality of facial follicles of an individual, an additive, and a delivery carrier designed to be applied to the individual, wherein the delivery carrier is further configured to enhance stability of the vasodilator and the additive.

17 Claims, 5 Drawing Sheets

| Vasodilator | | | Additive | | | | Additional Agents |
|---|---|---|---|---|---|---|---|
| | terpenes | stabilizers | emulsifiers | | propellants | moisturizer | |
| minoxidil | menthol | tris(2,4-di-tert-butylphenyl)phosphite | amphiphilic surfactants | | nitrous oxides | petrolatum | color elements |
| benazepril | eucalyptol | Salpn | lecithin | | dimethyl ether | hydrocarbons | texture elements |
| captopril | limonene | benzophenone | soy lecithin | | alkanes | petroleum jellies | ionic liquids |
| enalapril | terpenoids | benzotriazole | mucilage | | butane | soft paraffins | room-temperature ionic liquids |
| fosinopril | eicosenoic acid | polysorbate 60 | sodium phosphate | | butylated hydroxytoluene | multi-hydrocarbons | |
| lisinopril | erucic acid | stearyl alcohol | monoglyceride | | cetyl alcohol | jojoba oil | |
| moexipril | oleic acid | cetyl alcohol | diglyceride | | isobutane | coconut oil | |
| perindopril | palmitic acid | citric acid | sodium stearoyl lactylate | | propane | palmitic acid | |
| quinapril | monoterpenoids | dehydrated alcohol | diacetyl tartaric acid ester monoglyceride | | methane | palmitoleic acid | |
| ramipril | peppermint oil | lactic acid | diacetyl tartaric acid ester monoglyceride | | | stearic acid | |
| trandolapril | | glycol | cellulose | | | oleic acid | |
| azilsartan | | glycerin | sodium caseinate | | | arachidic acid | |
| candesartan | | oxygen scavengers | polysorbate 20 | | | 11-eicosenoic acid | |
| eprosartan | | antiozonants | ceteareth 20 | | | behenic acid | |
| irbesartan | | sequestrants | detergents | | | erucic acid | |
| telmisartan | | ultraviolet stabilizers | | | | lignoceric acid | |
| valsartan | | | | | | caprylic acid | |
| losartan | | | | | | capric acid | |
| olmesartan | | | | | | lauric acid | |
| amlodipine | | | | | | myristic acid | |
| clevidipine | | | | | | | |
| diltiazem | | | | | | | |
| felodipine | | | | | | | |
| isradipine | | | | | | | |
| nicardipine | | | | | | | |
| nimodipine | | | | | | | |
| nisoldipine | | | | | | | |
| verapamil | | | | | | | |
| nitroglycerin | | | | | | | |
| isosorbide mononitrate | | | | | | | |
| isosorbide dinitrate | | | | | | | |
| hydralazine | | | | | | | |
| fenoldopam | | | | | | | |
| nitroprusside | | | | | | | |

*FIG. 3*

COMPOSITION FOR STIMULATING FACIAL HAIR GROWTH AND METHODS OF MANUFACTURING A COMPOSITION FOR STIMULATING FACIAL HAIR GROWTH

CROSS-REFERENCE TO RELATED APPLICATIONS

This application claims the benefit of priority of U.S. Provisional Application No. 63/216,712 filed on Jun. 30, 2021, and entitled "COMPOSITION FOR STIMULATING FACIAL HAIR GROWTH", which is incorporated by reference herein in its entirety.

FIELD OF THE INVENTION

The present invention generally relates to the field of follicular stimulation. In particular, the present invention is directed to a composition for stimulating facial hair growth.

BACKGROUND

Numerous individuals struggle to grow and/or develop facial hair throughout their life. This is further complicated by the lack of understanding in the factors responsible for facial hair and/or follicular growth.

SUMMARY OF THE DISCLOSURE

In an aspect, a composition for stimulating facial hair growth includes a vasodilator including a medication that stimulates cell proliferation of a plurality of facial follicles of an individual, an additive, and a delivery carrier designed to be applied to the individual, wherein the delivery carrier is further configured to enhance stability of the vasodilator and the additive.

In another aspect, a method of manufacturing a composition for stimulating facial hair growth includes: receiving a vasodilator including a medication that stimulates cell proliferation of a plurality of facial follicles of an individual, receiving an additive, combining the vasodilator and the additive to create a liquid phase composition, and designing a delivery carrier to be applied to a user, wherein the delivery carrier is further configured to enhance stability of the vasodilator and the additive and comprises a pad-based applicator configured to expel the liquid phase composition.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 3 is a block diagram illustrating an exemplary embodiment of ingredients contained within composition of matter;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to a composition for stimulating facial hair growth. In an embodiment, this disclosure can include a vasodilator configured to include a medication. Aspects of the present disclosure can be used to include an additive that enhances absorption of the vasodilator. Aspects of the present disclosure can also be used to include a delivery carrier that can be configured to be applied to the individual. This is so, at least in part, because the delivery carrier enhances the stability and delivery of the vasodilator and the additive. Aspects of the present disclosure allow for the practical application of stimulating facial hair growth to allow an individual to grow and/or develop facial hair. Exemplary embodiments illustrating aspects of the present disclosure are described below in the context of several specific examples.

Figure 1:
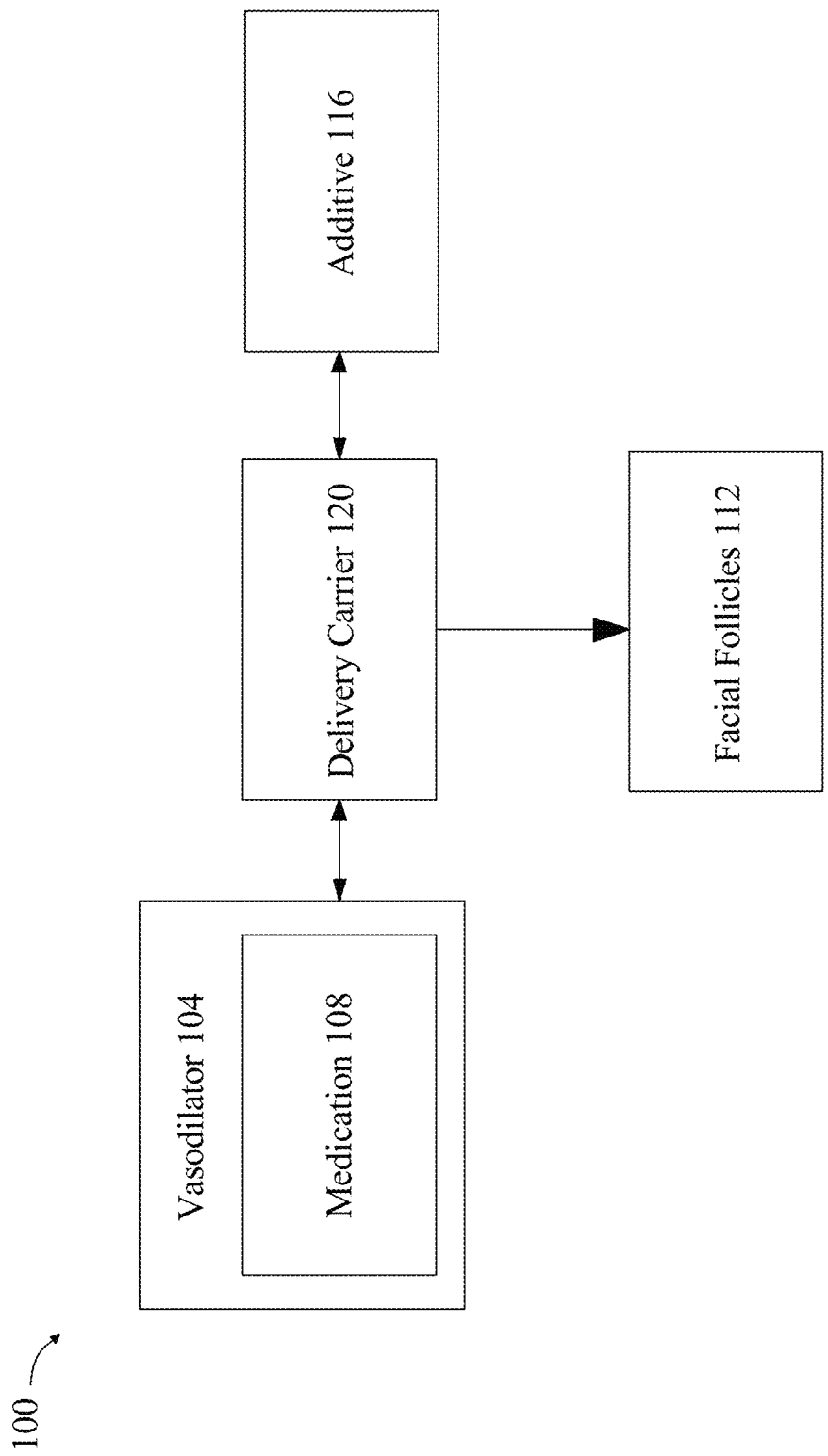
FIG. 1 is a block diagram illustrating an exemplary embodiment of a composition for stimulating facial hair growth.

Referring now to FIG. 1, a composition 100 for stimulating facial hair growth is illustrated. As used in this disclosure "facial hair" is hair and/or follicles that grows on an individual. In an embodiment, and without limitation, facial hair may include one or more hairs and/or follicles that grow along an individual's chin, cheeks, upper lip region, neck, and the like thereof. In an embodiment, and without limitation, facial hair may grow on an individual as a function of puberty. As used in this disclosure "puberty" is the process of physical changes through which a child's body matures into an adult body. For example, puberty may include one or more hormonal signals and/or processes that result in physiological changes of a human body. Additionally or alternatively, facial hair may include one or more facial hair patterns. As used in this disclosure a "facial hair pattern" is a style of a facial hair on an individual's body. For example, and without limitation, facial hair pattern may include a moustache style, such as but not limited to a "Fu Manchu," English moustache, handlebar moustache, imperial mustache, "Dali" moustache, chevron mustache, pyramid moustache, lampshade moustache, painter's brush, horseshoe moustache, pencil moustache, toothbrush moustache, walrus moustache, Hungarian moustache, and the like thereof. As a further non-limiting example, facial hair pattern may include a beard style, such as but not limited to a goat patch, goatee, "Zappa," Balbo, anchor beard, soul patch, "Van Dyke" beard, and the like thereof. As a further non-limiting example, facial hair pattern may include a partial beard style, such as but not limited to a chin curtain, chinstrap beard, designer stubble, friendly muttonchops, hulihee, circle beard, mutton chops, neckbeard, Shenandoah, sideburns, side whiskers, and the like thereof. As a further non-limiting example, facial hair pattern may include a full-beard style such as but not limited to a "Verdi" beard, "Garibaldi" beard, forkbeard, ducktail, "Ned Kelly" beard, and the like thereof.

Still referring to FIG. 1, composition 100 includes a vasodilator 104. As used in this disclosure a "vasodilator" is a product that promotes the dilation of at least a blood vessel of an individual. In an embodiment, and without limitation, vasodilator 104 may include one or more products that interact with an individual such that a relaxation of smooth muscle surrounding blood vessels occurs. In another embodiment, and without limitation, vasodilator 104 may include one or more products that lower intracellular calcium concentrations of an individual. In an embodiment, and without limitation, vasodilator 104 may include a product that changes the resting membrane potential of a cell to lower the concentration of the intracellular calcium as a function of modulating voltage-sensitive calcium channels in the plasma membrane of the cell. In an embodiment, and without limitation, vasodilator 104 may include one or more products that dephosphorylate myosin. In an embodiment and without limitation, vasodilator 104 may include one or more products that stimulate adrenergic receptors to elevate levels of cAMP and/or protein kinase A. In another embodiment, and without limitation, vasodilator 104 may include one or more products that stimulate protein kinase G. In another embodiment, and without limitation, vasodilator 104 may include one or more products that inhibit PDE5. In another embodiment, and without limitation, vasodilator 104 may include one or more products that open potassium channels located along the cell membrane. Additionally or alternatively, vasodilator 104 may be configured to be 0-5% weight/volume of composition 100. For example, and without limitation, vasodilator 104 may be configured to compose 3.2% weight/volume of composition 100. As a further non-limiting example, vasodilator 104 may be configured to be 1.1% weight/volume of composition 100.

In an embodiment, and still referring to FIG. 1, vasodilator 104 may be configured to enhance a permeation rate. As used in this disclosure a "permeation rate," is a measurement of the concentration of an analyte and/or substance that permeates a solid and/or tissue over a period of time, and wherein a period of time is a measurement of time such as, but not limited to, seconds, minutes, hours, days, weeks, years, and the like thereof. For example, and without limitation, additive may increase the permeation rate from 3.7 μg/cm² h¹ to 6.9 μg/cm² h¹. In an embodiment, and without limitation permeation rate may be enhanced as a function of calculating a permeation model. As used in this disclosure a "permeation model" is a model that outputs an estimated permeation of an analyte and/or substance across a solid and/or tissue non-invasively. In an embodiment, permeation model may include an algorithm comprising Fick's first law of diffusion, wherein Fick's first law of diffusion may be calculated by:

$$J = -D\frac{\partial \varphi}{\partial x}$$

wherein, J is the diffusion and/or permeation of the analyte and/or substance, D is the diffusion coefficient and/or mass diffusivity, φ is the concentration of the substance and/or analyte, and x is the position and/or length of diffusion and/or distance required to be traveled. In an embodiment, permeation model may comprise an algorithm comprising a modified Fick's first law of diffusion, wherein a modified Fick's first law of diffusion may be calculated by:

$$J = -D\frac{(C_2 - C_1)}{\delta}$$

wherein, $C_1$ is the concentration of a first analyte, $C_2$ is the concentration of a second analyte, and δ is the thickness of the solid and/or tissue. In an embodiment, and without limitation, vasodilator 104 may be configured to enhance permeation rate of a gas. As used in this disclosure a "gas" is a substance and/or matter in a state which will expand freely in a volume. For example, a gas may comprise one or more substances such as oxygen, argon, nitrogen, and the like thereof.

In an embodiment, and without limitation, vasodilator 104 may be configured to enhance a permeation rate of a nutrient. As used in this disclosure a "nutrient" is a substance that produces a source of energy to a cell and/or organism such that the cell and/or organism may grow, and/or reproduce. As a non-limiting example, nutrient may include, without limitation, a carbohydrate, such as glucose, sucrose, ribose, amylose, amylopectin, maltose, galactose, fructose, lactose, and the like thereof. Nutrient may include, without limitation, a protein, such as a standard amino acid, wherein a standard amino acid includes, but is not limited to, alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine, valine, and the like thereof. Nutrient may include without limitation a fat, such as a saturated fatty acid, monounsaturated fatty acid, polyunsaturated fatty acid, essential fatty acid, and the like thereof. Nutrient may include, without limitation, a vitamin, wherein a vitamin includes vitamins A, $B_1$, $B_2$, $B_3$, $B_5$, $B_6$, $B_7$, $B_9$, $B_{12}$, C, D, E, K, and the like thereof. Nutrient may include, without limitation, a mineral, such as potassium, chlorine, sodium, calcium, phosphorous, magnesium, iron, zinc, manganese, copper, iodine, chromium, molybdenum, selenium, cobalt, and the like thereof. Nutrient may include, without limitation, a hormone, wherein a hormone includes hormones such as, but not limited to, testosterone, dihydrotestosterone, dehydroepiandrosterone, androstenedione, progesterone, estriol, estradiol, estrone and the like thereof.

Still referring to FIG. 1, vasodilator 104 is configured to include a medication 108. As used in this disclosure a "medication" is a substance used for a medical treatment of a physiological process. For example, and without limitation, medication 108 may include one or more drugs and/or pharmaceuticals. For example, and without limitation, medication 108 may include one or more angiotensin-converting enzyme inhibitors such as, but not limited to, benazepril, captopril, enalapril, fosinopril, lisinopril, moexipril, perindopril, quinapril, ramipril, trandolapril. As a further non-limiting example, medication 108 may include one or more angiotensin receptor blockers such as, but not limited to azilsartan, candesartan, eprosartan, irbesartan, telmisartan, valsartan, losartan, olmesartan, and the like thereof. As a further non-limiting example, medication 108 may include one or more calcium channel blockers such as, but not limited to, amlodipine, clevidipine, diltiazem, felodipine, isradipine, nicardipine, nimodipine, nisoldipine, verapamil, and the like thereof. As a further non-limiting example, medication 108 may include one or more nitrates such as, but not limited to nitroglycerin, isosorbide mononitrate, isosorbide dinitrate, hydralazine, fenoldopam, nitroprusside, and the like thereof.

Still referring to FIG. 1, medication 108 is configured to stimulate cell proliferation of a plurality of facial follicles 112 of an individual. As used in this disclosure "cell proliferation" is a process that increases a number of cells of an individual. For example, and without limitation, cell proliferation may include one or more cell growths and/or cell divisions to produce two daughter cells, wherein a "daughter cell," as used herein, is a cell that originates as a function of a parent cell growing and dividing to two smaller cells. As a further non-limiting example, cell proliferation may include a process that leads to an exponential increase in a cell magnitude and/or cell number. As a further non-limiting example, cell proliferation may include one or more processes that are regulated as a function of a signal transduction and/or cell-cell communicative pathway. As used in this disclosure a "facial follicle" is an organ located in the skin of the face of an individual. In an embodiment, and without limitation facial follicle 112 may reside in the dermal layer of the skin of an individual. In another embodiment, facial follicle 112 may be composed of up to 20 distinct cell types. For example, and without limitation, facial follicle 112 may be composed of papilla cells, hair matrix cells, root sheath cells, cuboid cells, internal cuticle cells, stem cells, infundibulum cells, arrector pili cells, sebaceous cells, apocrine sweat cells, and the like thereof. In another embodiment, and without limitation, facial follicle 112 may regulate the growth of hair as a function of a complex interaction between hormones, neuropeptides, and immune cells. In another embodiment, facial follicle 112 may include one or more follicular phases, wherein a follicular phase is a sequential stage denoting the cycle of growth of a hair and/or hair follicle as described below, in reference to FIG. 2. For example, and without limitation, medication 108 may be configured to promote a telogenic phase to shed facial follicle 112 as described below, in reference to FIG. 2. As a further non-limiting example medication 108 may be configured to promote an anagenic phase to proliferate facial follicle 112 as described below, in reference to FIG. 2. The present invention may be used to enhance stimulation of facial hair growth of the trans male population.

In an embodiment, and still referring to FIG. 1, medication 108 may comprise minoxidil. As used in this disclosure "minoxidil" is a nitrate medication comprising a 2,4-diamino-6-piperidinopyrimidine 3-oxide structure. In an embodiment and without limitation, minoxidil may be a medication capable of reducing blood pressure of an individual. As a further non-limiting example, minoxidil may be a medication capable of reducing and/or reversing hair loss of an individual. As a further non-limiting example, minoxidil may be a medication capable of stimulating hair growth of an individual. Additionally or alternatively, medication 108 may be configured to hyperpolarize a cell membrane of a cell. As used in this disclosure "hyperpolarizing" is a process of altering and/or modifying a cell membrane potential to increase the amount of negativity of the cell membrane. For example, and without limitation, hyperpolarizing a cell membrane may include increasing the amount of negativity of a cell membrane from −50 mV to −80 mV. As a further non-limiting example, hyperpolarizing a cell membrane may include increasing the amount of negativity of a cell membrane from −70 mV to −90 mV.

In an embodiment, and still referring to FIG. 1, medication 108 may comprise finasteride. As used in this disclosure, "finasteride" is a 5-alpha reductase inhibitor that blocks the conversion of testosterone to dihydrotestosterone (DHT). In an embodiment, and without limitation, finasteride may be a medication capable of promoting hair growth and preventing further hair loss of an individual. Finasteride may be present between 0.01-3% of the weight to volume ratio of the composition 100. In an embodiment, finasteride may be 0.2% of the weight to volume ratio of the composition 100. In another embodiment, finasteride may be 2% of the weight to volume ratio of the composition 100. In another embodiment, finasteride may be 0.01% of the weight to volume ratio of the composition 100.

Still referring to FIG. 1, composition 100 comprises an additive 116. As used in this disclosure an "additive" is a substance and/or product that improves and/or preserves the effect of vasodilator 104. In an embodiment, and without limitation, additive 116 may comprise a terpene. As used in this disclosure a "terpene" is an unsaturated hydrocarbon consisting of the chemical composition $(C_5H_8)_n$. For example, and without limitation, terpene may comprise one or more monoterpenes, sesquiterpenes, diterpenes, and the like thereof. As a further non-limiting example, terpene may include, without limitation, menthol, eucalyptol, limonene, terpenoids, eicosenoic acid, erucic acid, oleic acid, palmitic acid, monoterpenoids, peppermint oil, etc. In an embodiment, and without limitation, terpene may increase a disease resistance. In another embodiment, and without limitation, terpene may increase cell growth. In another embodiment, and without limitation, terpene may produce an aromatherapeutic effect. In another embodiment, and without limitation terpene may enhance an absorption of one or more components of composition 100. As used in this disclosure an "absorption" is a physical process by which vasodilator 104 enters tissue and/or cells. In an embodiment and without limitation, absorption may be calculated as a function of a partition coefficient, wherein a "partition coefficient," as used herein, is the ratio of concentration of substances and/or analytes in composition 100 and concentration of substances and/or analytes in cells and/or tissues. For example, and without limitation partition coefficient may be calculated by:

$$\frac{[x]_1}{[x]_2} = K_{N(x,12)}$$

wherein, $K_{N(x,12)}$ is the partition coefficient, $[x]_1$, is the concentration of a first analyte and/or substance, and $[x]_2$, is the concentration of a second analyte and/or substance. In an embodiment, and without limitation, partition coefficient may be modified and/or varied as a function of temperature. For example, and without limitation, as temperature increases partition coefficient may increase. As a further non-limiting example, as temperature decreases partition coefficient may decrease. In an embodiment, and without limitation, concentration of the first analyte and/or substance and/or second analyte and/or substance may be calculated as a function of an ideal gas law, wherein an "ideal gas law," is an equation to calculate the state of a gas and is calculated by:

$$PV = nRT$$

wherein, P is the pressure, V is the volume, n is the amount of a substance and/or analyte, R is the ideal gas constant, and T is the temperature.

In an embodiment, and still referring to FIG. 1, additive 116 may comprise a stabilizer. As used in this disclosure a "stabilizer" is a substance and/or analyte that prevents degradation of composition 100. For example, and without limitation, stabilizer may include tris(2,4-di-tert-butylphenyl) phosphite. As a further non-limiting example, stabilizer may include Salpn. Salpn as used in this disclosure is defined as a chelating ligand, known by its proper name N,N'-bis(salicylidene)-1,2-propanediamine. As a further non-limiting example, stabilizer may include benzophenone and/or benzotriazole. As a further non-limiting example, stabilizer may include polysorbate 60. As a further non-limiting example, stabilizer may include stearyl alcohol, cetyl alcohol, citric acid, dehydrated alcohol, lactic acid, and the like thereof. As a further non-limiting example, stabilizer may include glycol. As a further non-limiting example, stabilizer may include glycerin. As a further non-limiting example, stabilizer may include oxygen scavengers. As a further non-limiting example, stabilizer may include radical scavengers. As a further non-limiting example, stabilizer may include antiozonants. As a further non-limiting example, stabilizer may include sequestrants. As a further non-limiting example, stabilizer may include ultraviolet stabilizers. In an embodiment, and without limitation, additive 116 may comprise an emulsifier. As used in this disclosure an "emulsifier" is a substance and/or analyte that stabilizes an emulsion. In an embodiment, and without limitation, emulsifier may stabilize an emulsion as a function of increasing a kinetic stability. In another embodiment, and without limitation, emulsifier comprise one or more amphiphilic surfactants. As used in this disclosure an "amphiphilic surfactant" is a compound that has a polar hydrophilic portion and a non-polar hydrophobic portion. In an embodiment, and without limitation, amphiphilic surfactants may produce one or more oil-in-water emulsions and/or water-in-oil emulsions. In an embodiment, and without limitation, emulsifier may comprise lecithin, soy lecithin, mucilage, sodium phosphate, monoglyceride, diglyceride, sodium stearoyl lactylate, diacetyl tartaric acid ester monoglyceride, diacetyl tartaric acid ester diglyceride, cellulose, sodium caseinate, and the like thereof. In another embodiment, and without limitation, emulsifier may comprise polysorbate 20, ceteareth 20, detergents, and the like thereof.

In an embodiment, and still referring to FIG. 1, additive 116 may comprise a propellant. As used in this disclosure a "propellant" is a substance and/or chemical that produces a movement of a fluid and/or substance. For example, and without limitation, propellant may comprise one or more substances and/or analytes that aid in moving composition from a first location to a second location. In an embodiment, and without limitation propellant may comprise an aerosol that escapes a first location to expel composition 100 and/or move composition 100 from the first location to a second location. In an embodiment, and without limitation, propellant may include one or more analytes and/or substances such as nitrous oxide, dimethyl ether, alkanes, butane, butylated hydroxytoluene, cetyl alcohol, isobutane, propane, methane, and the like thereof. Additionally or alternatively, additive 116 may be comprise a moisturizer. As used in this disclosure a "moisturizer" is a substance and/or analyte that regulates water content of a tissue and/or cell. In an embodiment, and without limitation moisturizer may modify one or more rates of water loss and/or transepidermal water loss. In another embodiment, and without limitation, moisturizer may protect a tissue and/or cell as a function of preventing excessive water loss that may lead to brittle and/or rigid tissues and/or cells. In an embodiment, and without limitation, moisturizer may include an occlusive. As used in this disclosure an "occlusive" is a substance and/or chemical that prevents water and/or moisture from escaping. In an embodiment and without limitation, occlusive may include a petrolatum such as, but not limited to, hydrocarbons, petroleum jellies, soft paraffins, multi-hydrocarbons, and the like thereof. In another embodiment and without limitation, occlusive may include one or more oils such as, but not limited to jojoba oil, coconut oil, and the like thereof. For example, and without limitation, jojoba oil may comprise one or more fatty acids such as, but not limited to, palmitic acid, palmitoleic acid, stearic acid, oleic acid, arachidic acid, 11-eicosenoic acid, behenic acid, erucic acid, lignoceric acid, nervonic acid, and the like thereof. As a further non-limiting example, coconut oil may comprise one or more fatty acids such as, but not limited to, caprylic acid, capric acid, lauric acid, myristic acid, palmitic acid, oleic acid, and the like thereof.

In an embodiment, and still referring to FIG. 1, moisturizer may comprise a humectant. As used in this disclosure a "humectant" is a substance and/or analyte that absorbs water. In an embodiment and without limitation, humectant may draw water from a first tissue and/or cell to a second tissue and/or cell. For example, and without limitation, humectant may draw water from the dermis portion of skin to the epidermis portion of skin. As a further non-limiting example, humectant may draw water from the air to the epidermis of the skin. Additionally or alternatively, moisturizer may comprise a temporary hydration agent, such as but not limited to water, aqueous solutions, saline, deionized water, distilled water, and the like thereof. In an embodiment, and without limitation, moisturizer may comprise one or more substances and/or analytes such as cetyl alcohol, cetearyl alcohol, cocoa butter, isopropyl myristate, isopropyl palmitate, lanolin, liquid paraffin, polyethylene glycol, shea butter, silicone oil, stearic acid, stearyl alcohol, castor oil, and the like thereof. In another embodiment, and without limitation, moisturizer may comprise an antioxidant, ceramide, emulsifier, fragrance, penetration enhancer, preservative, solvent, and the like thereof. In another embodiment, and without limitation, moisturizer may comprise a lotion, cream, ointment, bath oil, soap, soap substitute, and the like thereof.

In an embodiment, and without limitation, additive 116 may comprise a color element. As used in this disclosure a "color element" is a chemical and/or substance that modifies and/or alters a color of a follicle. For example, and without limitation, color element may include ammonia, wherein ammonia may open a cuticle layer of facial follicle 112. As a further non-limiting example, color element may comprise an oxidizing agent at varying concentrations to enter the opened cuticle layer of facial follicle 112 such that the oxidizing agent may react with facial follicle to alter and/or modify facial follicle 112. In another embodiment, and without limitation, color element may include an alkaline agent such as, but not limited to ethanolamine, sodium carbonate, and the like thereof to remove a natural pigment of facial follicle 112. In another embodiment, and without limitation, color element may include hydrogen peroxide to modify and/or alter a hair color of facial follicle 112 as a function of interacting with facial follicle 112. In another embodiment, and without limitation, color element may comprise one or more coloring products and/or pigmented dyes such as, but not limited to henna, indigo, blackcurrant, anthocyanin, and the like thereof. In another embodiment, and without limitation, color element may include one or more analytes and/or substances such as, but not limited to 1,4-diaminobenzene, 2,5-diaminotoluene, coupling agents such as, but not limited to, 1,3-diaminobenzene, 3-aminophenol, 5-amino-2-methylphenol, 1-naphthol, 2,5-diaminotoluene, 3-aminophenol, 4-chlororesorcinol, benzodioxoles, and the like thereof, and/or oxidants, such as, but not limited to, hydrogen peroxide, and the like thereof.

In an embodiment, and without limitation, additive 116 may comprise a texture element. As used in this disclosure a "texture element" is a substance and/or analyte that modifies and/or alters a texture of a hair. In an embodiment, and without limitation, additive 116 may be comprised of a texture element that converts one or more textures of hair from a first texture to a second texture. For example, and without limitation, texture element may modify a fine texture, wherein a "fine texture," as used herein is a texture that is fragile as a function of a hair that is comprised of a cortex layer and a cuticle layer, to a medium texture, wherein a "medium texture," as used herein is a texture that is malleable as a function of a hair that is comprised of a cortex layer, a cuticle layer, and a thin medulla layer. As a further non-limiting example, texture element may modify a medium texture to a thick texture, wherein a "thick texture," as used herein is a texture that is thick and/or coarse as a function of a hair that is comprised of a cortex layer, a cuticle layer, and a thick medulla layer. In an embodiment, and without limitation, thick texture may include a texture that produces an impression of a thicker facial hair style. As a further non-limiting example, thick texture may be more tolerant to heat, styling products, hair dye, breakage, and the like thereof. Additionally or alternatively, additive 116 may comprise an acid such as, but not limited to, L-ascorbic acid. In an embodiment, and without limitation, additive 116 may comprise an amino acid such as, but not limited to L-Carnitine.

Still referring to FIG. 1, composition 100 comprises a delivery carrier 120. As used in this disclosure a "delivery carrier" is a component that allows composition 100 to be applied to facial follicle 112. Delivery carrier 120 is configured to enhance stability of vasodilator 104 and/or additive 116. In some embodiments, delivery carrier 120 may increase a delivery of composition 100 to facial follicle 112. A stability of delivery carrier 120 may improve a patient adherence to using composition 100. As used in this disclosure a "stability" is a measurable value denoting the magnitude of reactivity of a compound. For example, and without limitation, stability may denote that vasodilator 104 has a high stability as a function of a low Gibbs Free Energy. As a further non-limiting example, stability may denote that additive 116 has a low stability as a function of a high Gibbs Free Energy. In an embodiment, and still referring to FIG. 1, delivery carrier 120 may dissolve and/or liquefy vasodilator 104 and/or additive 116 as a function of a solubility property, wherein solubility properties are described below. In another embodiment, and without limitation, delivery carrier 120 may suspend and/or mix vasodilator 104 and/or additive 116 as a function of an emulsion. In an embodiment, and without limitation, delivery carrier 120 may suspend and/or mix vasodilator 104 and/or additive 116 as a function of a liposome, nanoliposome, nano-lipid sphere, transfersome, noisome, ethosome, nanovesicle, and the like thereof. In an embodiment, and without limitation, delivery carrier 120 may comprise an ionic liquid. As used in this disclosure an "ionic liquid" is a salt substance and/or analyte that is in a liquid state. In an embodiment, and without limitation, ionic liquid may comprise one or more substances such as, but not limited to, liquid electrolytes, ionic melts, ionic fluids, fused salts, liquid salts, ionic glasses, and the like thereof. In another embodiment, and without limitation, ionic liquid may comprise one or more liquids that comprise an organic cation and/or a substance and/or analyte that maintains a low lattice energy. In an embodiment, and without limitation, ionic liquid may be configured to reduce a propensity of a polymorphic structure of vasodilator 104. As used in this disclosure a "polymorphic structure" is a solid material comprising a plurality of crystal structures. For example, and without limitation polymorphic structure may include a solid substance and/or analyte that comprises a plurality of crystal structures such as α, β, γ, δ, and the like thereof phases. In an embodiment, and without limitation, ionic liquid may reduce the propensity of a polymorphic structure of vasodilator as a function a solubility property. As used in this disclosure a "solubility property" is a chemical property of a substance and/or analyte to dissolve a solute and/or analyte. For example, and without limitation, solubility property of ionic liquids may be diverse as a function of a common-ion effect, ionic strength element, solubility equilibrium, temperature, and the like thereof. Additionally, and in an embodiment, delivery carrier 120 may apply the vasodilator 104 uniformly to the skin of a human. Uniform application may allow for uniform hair growth. Application of the composition is discussed in further detail below.

Still referring to FIG. 1, ionic liquid may comprise a room-temperature ionic liquid. As used in this disclosure a "room-temperature ionic liquid" is an ionic liquid that exists in a liquid state at room temperature. For example, and without limitation, room-temperature ionic liquid may comprise one or more salts derived from 1-methylimidazole. For example, and without limitation, salts derived from 1-methylimidazole may include 1-alkyl-3-methylimidazolium, 1-ethyl-3-methyl, 1-butyl-3-methyl, 1-octyl-3-methyl, 1-decyl-3-methyl, 1-dodecyl-3-methyl-dodecyl, and the like thereof. As a further non-limiting example, salts derived from 1-methylimidazole may include 1-butyl-2,3-dimethylimidazolium, 1,3-di(N,N-dimethylaminoethyl)-2-methylimidazolium, 1-butyl-2,3-dimethylimidazolium, and the like thereof. In an embodiment, and without limitation, room-temperature ionic liquid may comprise one or more cations derived from pyridine such as, but not limited to 4-methyl-N-butyl-pyridinium, N-octylpyridinium, and the like thereof. In another embodiment, and without limitation, room-temperature ionic liquid may comprise one or more cations such as tetraethylammonium, tetrabutyl ammonium, phosphonium, and the like thereof cations. Additionally or alternatively, room-temperature ionic liquid may comprise one or more anions such as but not limited to tetrafluoroborate, hexafluorophosphate, bis-trifluoromethanesulfonimide, trifluoromethanesulfonate, dicyanamide, hydrogen sulphate, ethyl sulphate, and the like thereof. In an embodiment, and without limitation, ionic liquid may be comprised of a low-temperature ionic liquid, protic ionic liquid, poly-ionic liquid, magnetic ionic liquid, and the like thereof. In another embodiment, ionic liquids may increase transcellular transport as a function of a choline-based bioinspired ionic liquid, such as but not limited to, choline phenylalaninate. In another embodiment, ionic liquids may increase permeation rate as a function of an imidazole based ionic liquid such as, but not limited to, ionic liquids derived from 1-methylimidazole as described above.

For example, and without limitation, delivery carrier 120 may comprise a rollerball applicator. As used in this disclosure a "rollerball applicator" is a device and/or component that applies one or more substances to facial follicle 112 as a function of a rollerball. For example, and without limitation, rollerball applicator may include a device and/or component that stores composition 100 in a tube that has a first end and a second end, wherein the first end is blocked as a function of a cap and/or wall, and wherein the second end is blocked by a ball and/or sphere. In an embodiment, and without limitation, rollerball applicator may be configured to expel a liquid phase composition from the tube as a function of the ball and/or sphere rotating and/or rolling. For example, and without limitation, the ball may rotate, wherein the liquid phase composition may be expelled as a function of the ball drawing the liquid phase composition from the tube. Additionally or alternatively, delivery carrier 120 may comprise a foam. As used in this disclosure a "foam" is an object and/or substance that is formed as a function of trapping pockets of gas and/or liquid in a solid. For example, and without limitation, foam may comprise a closed-cell and/or open-cell foam as a function of the location of the gas pockets. As a further non-limiting example, foam may comprise a liquid foam that releases a gas pocket as a function of a manipulation and/or movement of the foam. In an embodiment, foam may store and/or stabilize composition 100 such that composition 100 may be easily applied to an individual's extremities, face, skin, and the like thereof. Additionally or alternatively, delivery carrier 120 may comprise one or more gels, ointments, creams, powders, lotions, pastes, balms, and the like thereof. Alternatively or additionally, delivery carrier 120 may include a spray applicator. A spray applicator may include a tube for storing composition 100. Tube may include any tube as discussed herein. A spray applicator may include a spray nozzle that facilitated a dispersion of composition 100 into a spray. A spray applicator may be configured to expel a liquid phase composition from the tube directly onto an individual/a facial follicle 112.

In another embodiment, delivery carrier 120 may comprise a pad-based applicator. As used in this disclosure, a "pad-based applicator" is a device and/or component that applies one or more substances to facial follicle 112 via a pad. For example, and without limitation, pad-based applicator may include an outer casing that may contain composition 100 along with a plurality of pads. Outer casing may have a first end and a second end, wherein the first end is blocked as a function of a wall, and wherein the second end is blocked by a cap that may be temporarily removed to access the pads within. In some embodiments, the cap may be a door, lid, hinged opening, sliding door, and the like. Outer casing may be in contact with a surface of a pad/pads. Outer casing may prevent the pad/pads and/or composition 100 from being in contact with external environments. In another embodiment, pad-based applicator may include a device and/or component that stores composition 100 and one or more pads in a sealed package. A sealed package may include a top wall and a bottom wall, wherein the pad/pads and composition 100 may be placed within. Top wall and a bottom wall may be adhered or otherwise joined together to form a compartment before the pad/pads and composition 100 may be placed inside. Package may be composed of a thin metal such as aluminum and/or a thin plastic such that the package is still flexible.

Continuing to reference FIG. 1, pad-based applicator may include a pad. The pad may be constructed from a flexible, pliant, soft material, such as cotton, polypropylene, nylon, viscose, flax, or the like. A pad may include hydrophilic materials and/or hydrophobic materials such as polyethylene terephthalate or polypropylene. Pad may include several layers of materials. In an embodiment, pad may include 3 layers of material. In another embodiment, pad may include 1 layer of material. A pad may be pre-soaked in composition 100 such that application of the composition 100 consists of applying the pad to an individual's extremities, face, skin, and the like thereof. Liquid-phased composition may be expelled from the pad, by way of application. The individual may apply a force to the pad such that the pad expels composition 100 to a desired location. In an embodiment, pad-based applicator may store and/or stabilize composition 100 such that composition 100 may be easily applied to an individual's extremities, face, skin, and the like thereof.

Figure 2:
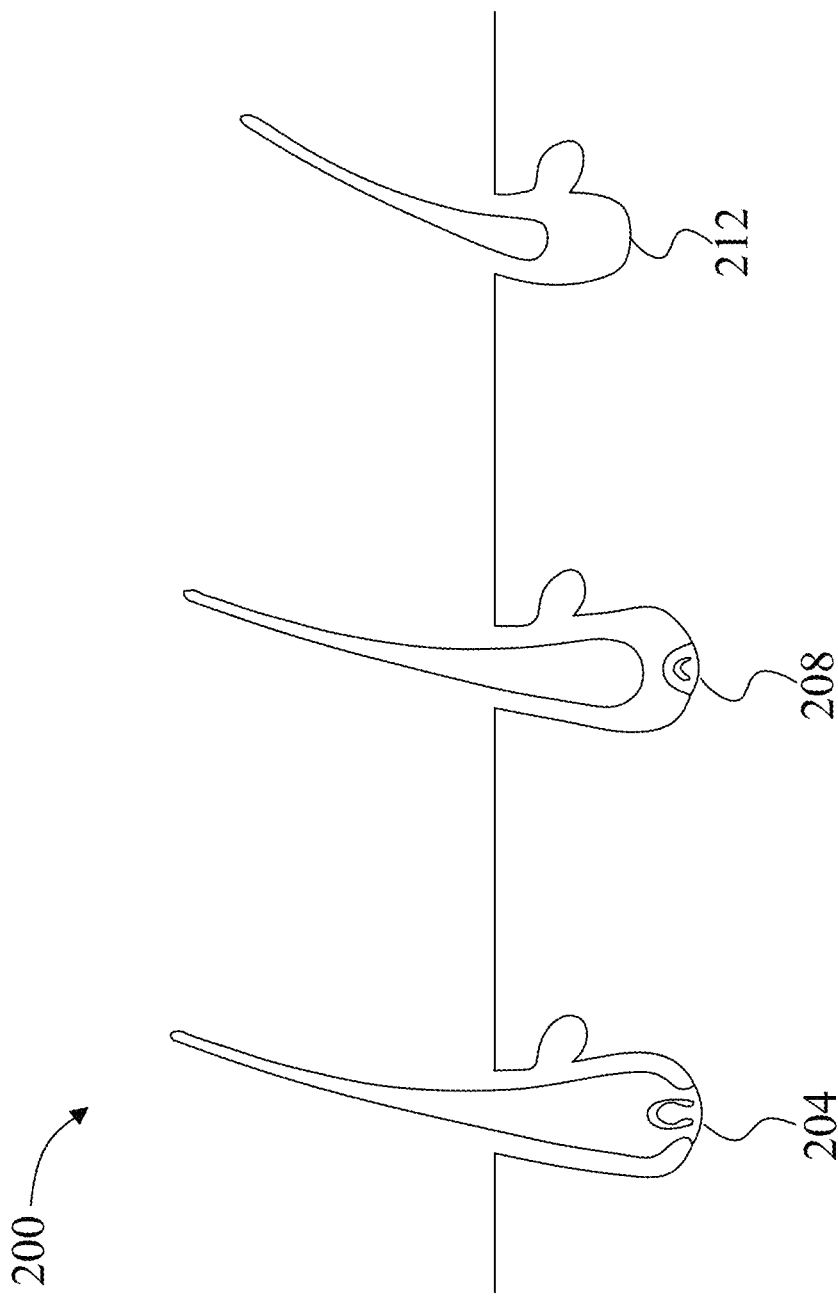
FIG. 2 is a diagrammatic representation of an exemplary embodiment of a follicular phase.

Referring now to FIG. 2, an exemplary embodiment 200 of a follicular phase is illustrated. As used in this disclosure a "follicular phase" is a sequential stage denoting the cycle of growth of a hair and/or hair follicle. In an embodiment, and without limitation, follicular phase may include an anagenic phase 204. As used in this disclosure an "anagenic phase" is a phase and/or time period wherein the follicle and/or hair grows and/or proliferates. In an embodiment, anagenic phase 204 may comprise a phase of active growth of a hair follicle. In another embodiment, anagenic phase 204 may comprise a phase wherein hair grows about 1 cm every 28 days. In another embodiment, anagenic phase 204 may extend from a range of time between 4 months to 8 years. Follicular phase may include a catagenic phase 208. As used in this disclosure a "catagenic phase" is a phase and/or time period wherein the hair and/or follicle converts to a club hair, wherein a "club hair," as used herein is an end product of final hair growth that features a bulb of keratin at the root tip of a hair strand. In an embodiment, and without limitation, catagenic phase 208 may include a phase wherein the hair follicle previously in contact with the lower portion of the hair becomes attached to a hair shaft. In another embodiment, catagenic phase 208 may include a phase wherein the blood supply from the hair follicle to the hair may be terminated and/or extinguished as a function of the loss of contact. In an embodiment, and without limitation, catagenic phase 208 may extend from a range of time between 2 weeks to 4 weeks. Follicular phase may include a telogenic phase 212. As used in this disclosure a "telogenic phase" is a phase and/or time period wherein the hair follicle is at rest. For example, and without limitation, telogenic phase 212 may include a phase wherein the club hair is shed and/or eliminated from the skin. In another embodiment, and without limitation, telogenic phase 212 may include a time herein a loss of hair may occur. In another embodiment, and without limitation, telogenic phase 212 may extend from a range of between 3 months to 9 months.

In an embodiment, and still referring to FIG. 2, medication 108 may stimulate the proliferation of anagenic phase 204 as a function of a plurality of dosing concentrations. In an embodiment, and without limitation, medication 108 may be in a range of 0-5% weight/volume of composition 100. For example, and without limitation, medication 108 may be configured to compose 2.1% weight/volume of composition 100. As a further non-limiting example, vasodilator 104 may be configured to be 5.0% weight/volume of composition 100. In another embodiment, and without limitation, medication 108 may stimulate the proliferation of anagenic phase 204 as a function of a plurality of dosing frequencies. As used in this disclosure a "dosing frequency" is an amount of applications and/or doses that are provided to an individual at a specific concentration. For example, and without limitation, dosing frequency may denote that composition 100 should be applied every 1 day at a medication concentration of 1.7% weight/volume of composition 100. As a further non-limiting example, dosing frequency may denote that composition 100 should be applied every 30 minutes at a medication concentration of 4.2% weight/volume of composition 100.

Referring now to FIG. 3, an exemplary embodiment of ingredients 300 contained within composition 100 is illustrated. Composition 100 includes vasodilator 104, wherein vasodilator 104 includes any of the vasodilator 104 described above, in reference to FIGS. 1-2, and wherein vasodilator 104 may include but is not limited to any of the vasodilators contained within column 304. Vasodilator 104 may include but is not limited to minoxidil benazepril, captopril, enalapril, fosinopril, lisinopril, moexipril, perindopril, quinapril, ramipril, trandolapril, azilsartan, candesartan, eprosartan, irbesartan, telmisartan, valsartan, losartan, olmesartan, amlodipine, clevidipine, diltiazem, felodipine, isradipine, nicardipine, nimodipine, nisoldipine, verapamil, nitroglycerin, isosorbide mononitrate, isosorbide dinitrate, hydralazine, fenoldopam, nitroprusside, and the like thereof. Composition 100 includes an additive 116, wherein additive 116 includes any of the additive 116 as described above, in reference to FIGS. 1-2, and wherein additive 116 may include but is not limited to any of the additives contained within column 308. Additive 116 may include terpenes such as, but not limited to, menthol, eucalyptol, limonene, terpenoids, eicosenoic acid, eruic acid, oleic acid, palmitic acid, monoterpenoids, peppermint oil, and the like thereof. Additive 116 may include stabilizers such as, but not limited to, tris(2,4-di-tert-butylphenyl) phosphite, Salpn, benzophenone, benzotriazole, polysorbate 60, stearyl alcohol, cetyl alcohol, citric acid, dehydrated alcohol, lactic acid, glycol, glycerin, oxygen scavengers, antiozonants, sequestrants, ultraviolet stabilizers and the like thereof. Additive 116 may include emulsifiers such as, but not limited to amphiphilic surfactants, lecithin, soy lecithin, mucilage, sodium phosphate, monoglyceride, diglyceride, sodium stearoyl lactylate, diacetyl tartaric acid ester monoglyceride, diacetyl tartaric acid ester diglyceride, cellulose, sodium caseinate, polysorbate 20, ceteareth 20, detergents, and the like thereof. Additive 116 may include propellants such as, but not limited to nitrous oxides, dimethyl ether, alkanes, butane, butylated hydroxytoluene, cetyl alcohol, isobutane, propane, methane, and the like thereof. Additive 116 may include moisturizers such as, but not limited to, petrolatum, hydrocarbons, petroleum jellies, soft paraffins, multi-hydrocarbons, jojoba oil, coconut oil, palmitic acid, palmitoleic acid, stearic acid, oleic acid, arachidic acid, 11-eicosenoic acid, lignoceric acid, caprylic acid, capric acid, lauric acid, myristic acid, and the like thereof. Composition 100 includes an additional agent, wherein additional agents may include but are not limited to any of the additional agents contained within column 312. Additional agents may include but are not limited to color elements, texture elements, ionic liquids, room-temperature ionic liquids, L-Carnitine, L-ascorbic acid, and the like thereof.

Figure 4:
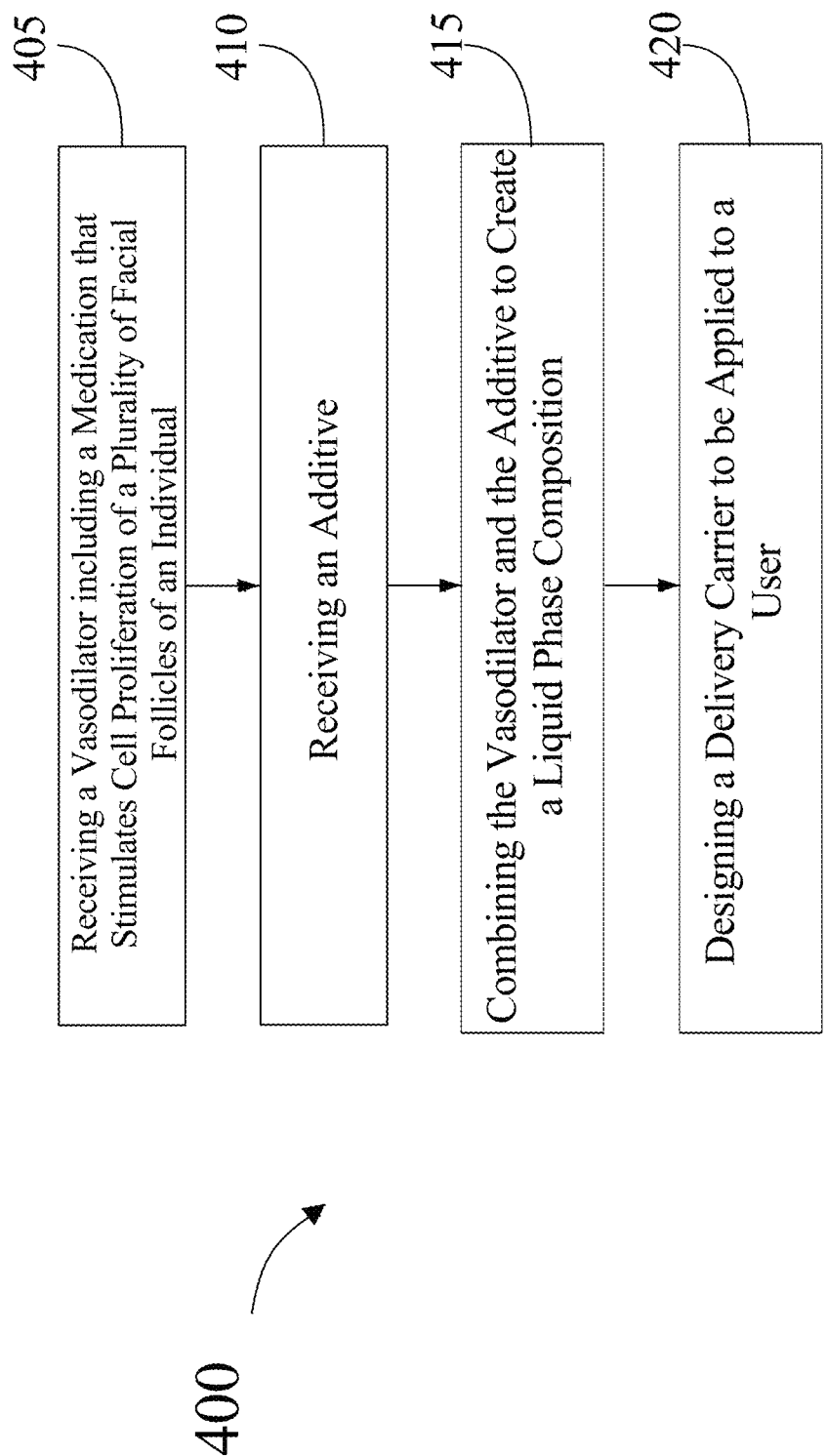
FIG. 4 is a block diagram illustrating an exemplary embodiment of a method of manufacturing a composition for stimulating facial hair growth.

Referring now to FIG. 4, a method 400 of manufacturing a composition for stimulating facial hair growth is shown. Step 405 of method 400 includes receiving a vasodilator including a medication that stimulates cell proliferation of a plurality of facial follicles of an individual. Vasodilator may include any vasodilator as described above. Step 410 of method 400 includes receiving an additive. Additive may include any additive as described above. Step 415 of method 400 includes designing a delivery carrier to be applied to a user, wherein the delivery carrier is further configured to enhance stability of the vasodilator and the additive and comprises a pad-based applicator configured to expel the liquid phase composition. Pad-based applicator may include any pad-based applicator as discussed herein.

Figure 5:
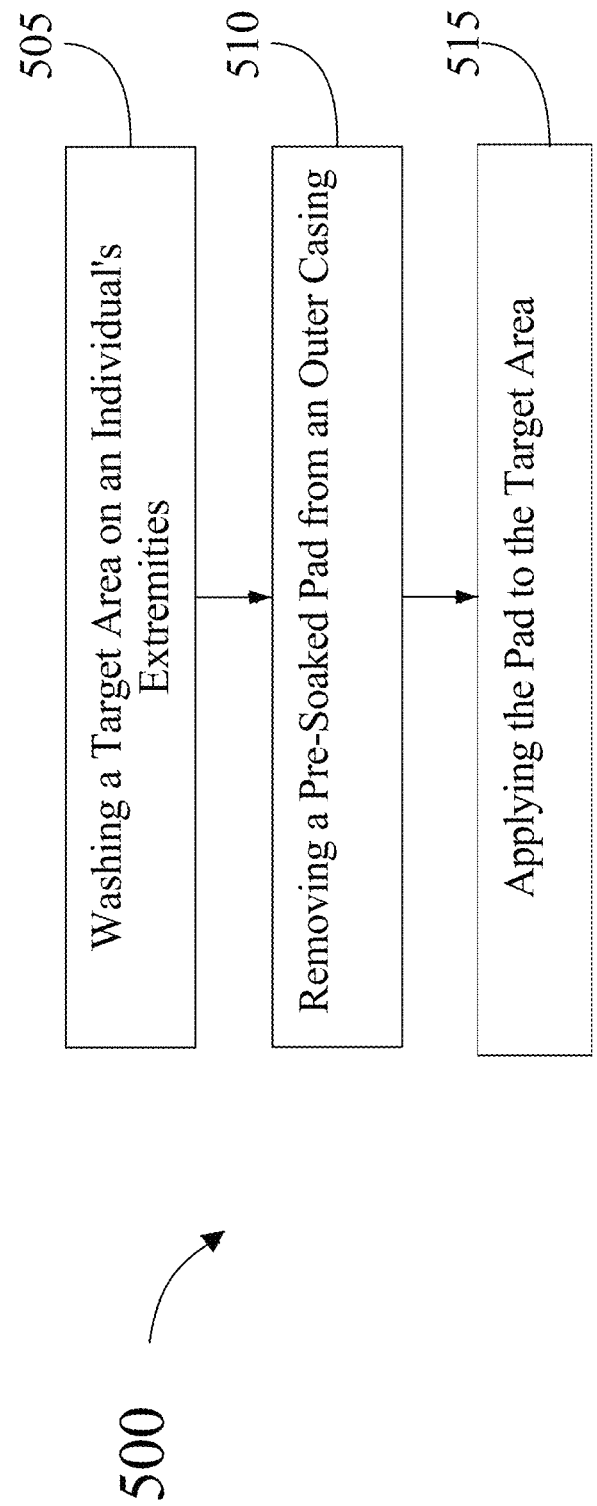
FIG. 5 is a block diagram illustrating an exemplary embodiment of a method of using pad-based applicator to stimulate hair growth.

Referring now to FIG. 5, a method 500 of using pad-based applicator to stimulate hair growth is shown. Step 505 of method 500 includes washing a target area on an individual's extremities where the target facial follicles are located. Washing may include washing with water. Water may include tap water, distilled water, filtered water, or the like. Step 510 of method 500 includes removing a pre-soaked pad, soaked in the composition, from an outer casing. Removing from an outer casing may include removing a cap from the outer casing. Cap may be used to seal the delivery carrier to protect the composition from external elements. Outer casing may be any outer casing as discussed herein. Composition may be any composition as discussed herein. Cap may be any cap as discussed herein. Step 515 of method 500 includes applying the pad to a target area such as individual's extremities, face, skin, and the like thereof, that has been washed. Applying the pad may include applying pressure onto the pad to the target area to dispose of the composition onto the target area. Pressure may be applied using the individual's fingers, which may be holding the pad. Pressure may be applied using alternate mechanisms, such as an applicator, which may include a stick, tongs, or the like.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve compositions according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A composition for stimulating facial hair growth, wherein the composition comprises:
   a vasodilator comprising a medication, wherein the medication comprises a first agent containing minoxidil, wherein the first agent is present between 0.01-5% of the weight to volume ratio of the composition;
   an additive comprising a color element and a stabilizer comprising a radical scavenger and an emulsifier comprising an amphiphilic surfactant, wherein the stabilizer added to the additive comprises N,N'-bis(salicylidene)-1,2-propanediamine; and
   a delivery carrier, wherein the delivery carrier is further configured to enhance stability of the first agent and the additive and comprises an applicator configured to deliver the composition.

2. The composition of claim 1, wherein the vasodilator further comprises a second agent comprising finasteride present between 0.01-3% of the weight to volume ration of the composition.

3. The composition of claim 1, wherein the vasodilator further comprises a medication comprising an angiotensin-converting enzyme inhibitor.

4. The composition of claim 3, wherein the medication is configured to promote a telegenic phase to shed the plurality of facial follicles and an anagenic phase to proliferate the plurality of facial follicles.

5. The composition of claim 3, wherein the medication is configured to hyperpolarize a cell membrane of a cell.

6. The composition of claim 1, wherein the vasodilator is configured to enhance a permeation rate.

7. The composition of claim 1, wherein the vasodilator is configured to enhance the permeation rate of a nutrient contained within the composition.

8. The composition of claim 1, wherein the additive comprises a terpene.

9. The composition of claim 8, wherein the terpene is configured to enhance absorption of the vasodilator.

10. The composition of claim 1, wherein the additive comprises an emulsifier comprising diglyceride.

11. The composition of claim 1, wherein the additive comprises a propellant comprising dimethyl ether.

12. The composition of claim 1, wherein the additive comprises a moisturizer.

13. The composition of claim 12, wherein the moisturizer includes a humectant comprising cetyl alcohol.

14. The composition of claim 12, wherein the moisturizer further comprises jojoba oil.

15. The composition of claim 12, wherein the moisturizer further comprises coconut oil.

16. The composition of claim 1, wherein the delivery carrier comprises an ionic liquid configured to reduce a propensity of a polymorphic structure of the vasodilator.

17. The composition of claim 16, wherein the ionic liquid comprises a room-temperature ionic liquid.

* * * * *